US00PP29327P2

(12) United States Plant Patent
Lambalk

(10) Patent No.: US PP29,327 P2
(45) Date of Patent: May 29, 2018

(54) ***HIBISCUS* 'SUMMER NIGHT'**

(50) Latin Name: *Hibiscus syriacus*
Varietal Denomination: Summer Night

(71) Applicant: Johannes Jacobus Maria Lambalk, Middenbeemster (NL)

(72) Inventor: Johannes Jacobus Maria Lambalk, Middenbeemster (NL)

(73) Assignee: Valkplant BV (NL)

( * ) Notice: Subject to any disclaimer, the term of this patent is extended or adjusted under 35 U.S.C. 154(b) by 0 days. days.

(21) Appl. No.: 15/530,766

(22) Filed: Feb. 24, 2017

(51) Int. Cl.
*A01H 5/02* (2018.01)

(52) U.S. Cl.
USPC ..... Plt./257
CPC ..... *A01H 5/02* (2013.01)

(58) Field of Classification Search
USPC ..... Plt./257
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Hibiscus* cultivar named 'SUMMER NIGHT' is disclosed, characterized by fully double purple flowers. Plants are compact and have flowers that will open in cold climates. The new variety is a *Hibiscus*, normally produced as an outdoor garden or container plant.

2 Drawing Sheets

Figure 1:
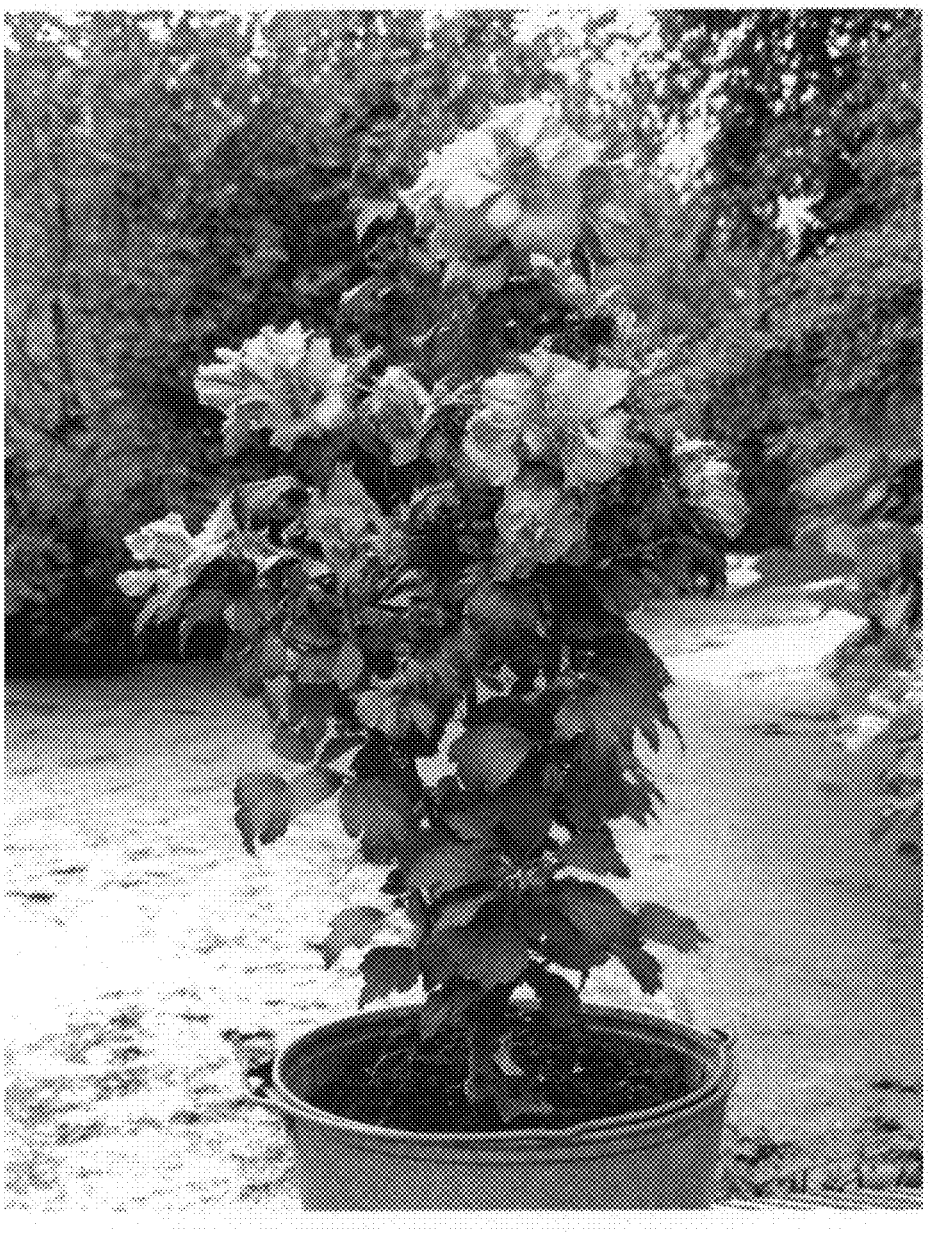

Latin name of the genus and species: *Hibiscus syriacus*.
Variety denomination: 'SUMMER NIGHT'.

BACKGROUND OF THE INVENTION

The new *Hibiscus* cultivar is a product of a planned breeding program conducted by the inventor in Middenbeemster The Netherlands. The objective of the breeding program was to produce new *Hibiscus syriacus* varieties with double flowers on dwarf plants. crossing resulting in this new variety was made during 2002.

The seed parent is the unpatented *Hibiscus syriacus* 'Oiseau Blue', the pollen parent is the proprietary variety 'Summer Holiday', filed concurrently (U.S. Plant patent application Ser. No. 15/530,764). The new variety was identified as a potentially interesting selection during 2005. Selection was made at a research nursery in Middenbeemster, The Netherlands.

Asexual reproduction of the new cultivar 'SUMMER NIGHT' was first performed in February 2014 at a commercial nursery in Hazerswoude, The Netherlands. Vegetative soft wood cuttings were grafted onto an unnamed, unpatented *Hibiscus syriacus* rootstock. Subsequent propagation has shown that the unique features of this cultivar are stable and reproduced true to type in 6 successive generations.

SUMMARY OF THE INVENTION

The cultivar 'SUMMER NIGHT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUMMER NIGHT' These characteristics in combination distinguish 'SUMMER NIGHT' as a new and distinct *Hibiscus* cultivar:

1. Double, purple flowers
2. Flowers will open in cold climates.
3. Compact plants.

PARENT COMPARISON

Plants of the new cultivar 'SUMMER NIGHT' are similar to plants of the seed parent variety in most horticultural characteristics, however, plants of the new cultivar 'SUMMER NIGHT' differ in the following;

1. The new variety has a flower colored more purple than blue, the seed parent has a blue flower.
2. The new variety has a double flower, the seed parent variety has a single flower.

Plants of the new cultivar 'SUMMER NIGHT' are similar to plants of the pollen parent variety in most horticultural characteristics, however, plants of the new cultivar 'SUMMER NIGHT' differ in the following;

1. The new variety has a purple flower, the pollen parent has a pink and white colored flower.

COMMERCIAL COMPARISON

Plants of the new cultivar 'SUMMER NIGHT' can be compared to the variety *Hibiscus* 'SHIMRR38', U.S. Plant Pat. No. 26,374. These varieties are similar in most horticultural characteristics however, 'SUMMER NIGHT' differs in the following:

1. Flowers of the new variety are double, flowers of this comparator are single.
2. Plants of the new variety have a very upright habit, plants of this comparator are more mounded.
3. Plants of the new variety are taller than plants of this comparator.

BRIEF DESCRIPTION OF THE PHOTOGRAPHS

The accompanying photograph in FIG. 1 illustrates in full color a typical plant of 'SUMMER NIGHT' grown in a 3 gallon pot.

Figure 2:
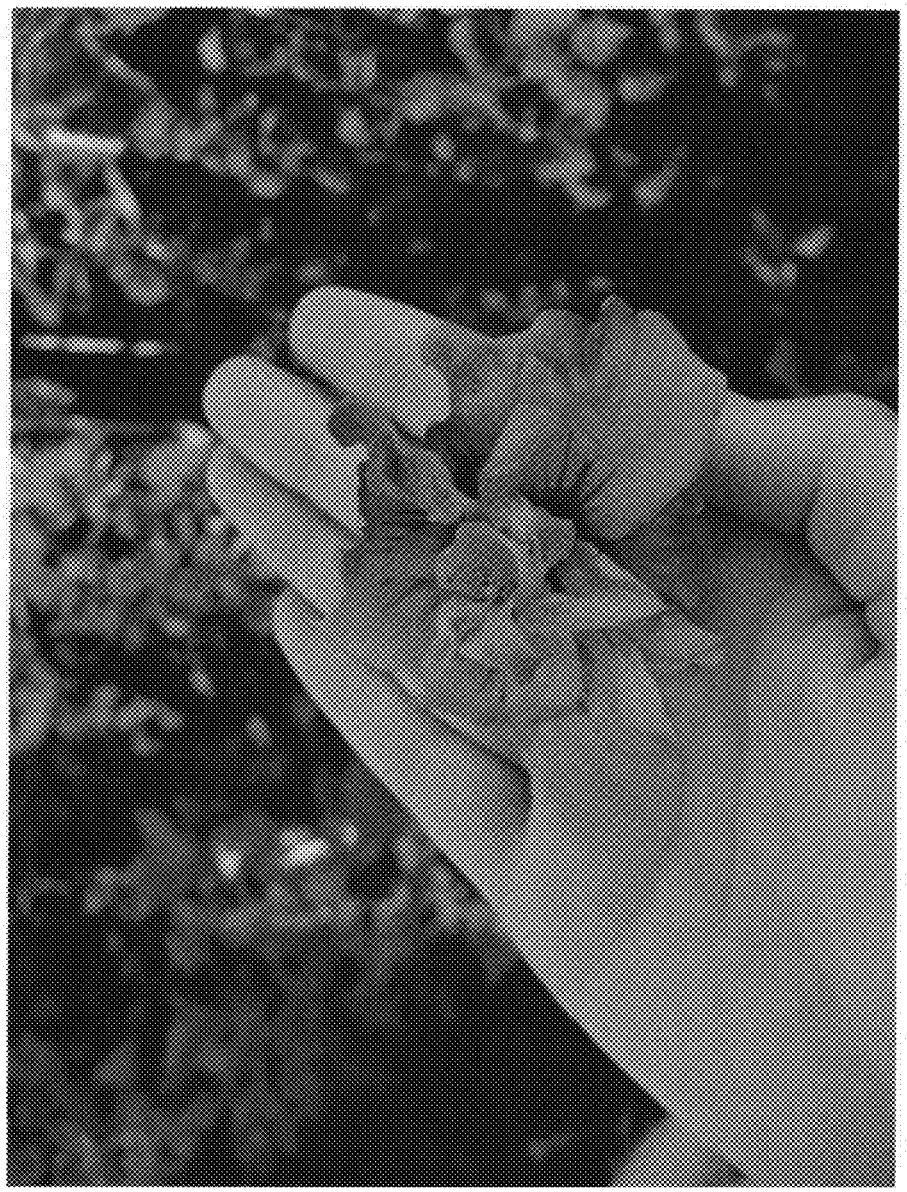

FIG. 2 illustrates in full color a typical flower of 'SUMMER NIGHT'. Age of the plant photographed is approximately 2 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'Summer Night' plants grown in a polyhouse in Grand Haven, Mich. Measurements were taken during late Summer. The plants were 2 years old in 3 gallon containers. The growing temperature ranged from approximately 18° C. to 27° C. during the day and 5° C. to 10° C. at night. Measurements and numerical values represent averages of typical plant types.

Botanical classification: *Hibiscus syriacus* 'SUMMER NIGHT'.

PROPAGATION

Time to initiate roots: 20 days at approximately 25° C.

Root description: Fibrous, medium root thickness. Tan/brown in color, not effectively measured with a color chart.

Time to produce a rooted young plant: About 90 days at 25° C.

PLANT

Plant type: Perennial shrub.

Age of plant described: Approximately 2 years old.

Growth habit: Upright, nearly columnar.

Pot size of plant described: 3 gallon pot.

Overall plant shape: Upright, nearly columnar.

Height: 42 cm.

Plant spread: 35 cm.

Plant vigor: Moderate.

Branching characteristics: Upright and compact. No basal branching. Very upright plant with branches at acute angles.

Length of primary lateral branches: Average range 5 to 25 cm.

Diameter of lateral branches: 4 mm.

Quantity of lateral branches: Average 7.

Stem:

- *Stem shape.*—Round.
- *Stem strength.*—Strong.
- *Color.*—Stem: Near RHS Yellow-Green 152B.
- *Texture.*—Glabrous.
- *Angle of attachment.*—Branches very upright, occurring at acute angles from center of plant.

Internode length: 4 cm on average.

FOLIAGE

Leaf:

- *Arrangement.*—Alternate, single.
- *Leaf shape.*—Ovoid, lobed.
- *Average length.*—8.5 cm.
- *Average width.*—6.5 cm.
- *Apex.*—Acute.
- *Base.*—Cuneate.
- *Margin.*—Crenate.
- *Texture of top surface.*—Smooth, waxy with prominent veins.
- *Texture of bottom surface.*—Smooth, waxy with prominent veins.
- *Color.*—Young foliage upper side: Near RHS Green 143A. Young foliage under side: Near RHS Yellow-Green 144B. Mature foliage upper side: Near RHS Green 143A. Mature foliage under side: Near RHS Yellow-Green 144B.
- *Venation.*—Pattern: Palmate. Color upper side: Near RHS Yellow-Green 144C. Color under side: Near RHS Yellow-Green 144C.
- *Petiole.*—Average Length: 2 cm. Diameter: 3 mm. Petiole color upper side: Near RHS Yellow-Green 144A. Petiole color lower side: Near RHS Yellow-Green 144B. Petiole Texture upper side: Pubescent. Petiole Texture lower side: Smooth.

FLOWER

Natural flowering season: Spring through Summer continuously.

Flowering form: Fully double, whorled.

Flower habit: Solitary, emerging from leaf axils.

Flower longevity on plant: About 4 days.

Quantity of flowers per plant: About 50 flowers and buds on a mature plant in full bloom.

Flower shape: Overall shape is a half dome.

Flower aspect: Upright and slightly outward.

Size:

- *Length.*—3 cm.
- *Diameter.*—6 cm.

Flower other characteristics:

- *Persistence.*—Self-cleaning.
- *Fragrance.*—Light, earthy.

Bud:

- *Shape.*—Spherical.
- *Length.*—Average 1.5 cm.
- *Diameter.*—Average 1.0 cm.
- *Color.*—Near Green 142B.

Petal:

- *Petal arrangement.*—Whorled and a thick central whorl of petaloids.
- *Number of petals per flower.*—5 large outer petals.
- *Fused.*—At base.
- *Petal shape.*—Obovate.
- *Petal base.*—Fused.
- *Margin.*—Entire, undulate.
- *Tip shape.*—Retuse.
- *Length.*—2 cm.
- *Width.*—3 cm.
- *Texture.*—Upper: Glabrous. Lower: Glabrous.
- *Appearance.*—Upper surface matte with glossy base. Lower surface matte.

Petal color:

- *When opening.*—Upper surface: Near Purple-Violet N80D. Lower surface: Near Purple N78B.
- *Fully opened.*—Upper surface: Near Purple-Violet N80D, basal blotch near Red-Purple 59B. Lower surface: Near Purple N78B.

*Fading to*.—Upper surface: Near Purple-Violet N80D, basal blotch near Red-Purple 59B. Lower surface: Near Purple N78B.

Petaloids:

*Arrangement*.—Thick central whorl of petaloids at the base of the style.

*Number of petaloids per flower*.—Average 30.

*Shape*.—Irregular orbicular or obovate.

*Base*.—Fused.

*Margin*.—Entire, undulate.

*Tip shape*.—Retuse.

*Length*.—Average 1.75 cm.

*Width*.—Average range 0.5 to 1.5 cm.

*Texture*.—Upper: Glabrous. Lower: Glabrous.

*Appearance*.—Upper surface matte with glossy base. Lower surface matte.

Petaloid color:

*When opening*.—Upper surface: Near Purple-Violet N80D. Lower surface: Near Purple N78B.

*Fully opened*.—Upper surface: Near Purple-Violet N80D, basal blotch near Red-Purple 59B. Lower surface: Near Purple N78B.

Calyx:

*Shape*.—Deltate.

*Length*.—7 mm.

*Diameter*.—1 cm.

Sepal:

*Arrangement*.—Rotate.

*Number*.—Average 4 to 5.

*Shape*.—Deltate.

*Tip*.—Acicular.

*Base*.—Truncate.

*Margin*.—Entire.

*Length*.—2 cm.

*Width*.—3 mm.

*Texture, upper*.—Smooth.

*Texture, lower*.—Smooth, waxy.

*Color*.—Upper surface: Near Green 137C. Under surface Near Green 137C.

Peduncle:

*Length*.—2 cm.

*Diameter*.—2 mm.

*Color*.—Near RHS Green 137C.

*Orientation*.—Straight.

*Strength*.—Strong.

*Texture*.—Softly pubescent.

REPRODUCTIVE ORGANS

Stamens:

*Number*.—Average 16, clustered and implanted in style, typical of *Hibiscus*.

*Filament length*.—7 mm.

*Filament color*.—Near Green-White 157D.

Anthers:

*Shape*.—Dorsifixed.

*Length*.—2 mm.

*Color*.—Near Green-White 157D.

*Pollen color*.—Near Green-White 157D.

*Pollen amount*.—Moderate.

Pistil:

*Number*.—6.

*Length*.—1.0 cm.

*Style*.—Length: 1.7 cm. Color: Near Green-White 157D.

*Stigma*.—Shape: Peltate. Color: Near Green White 157D.

*Ovary color*.—Near RHS Yellow-Green 150C.

OTHER CHARACTERISTICS

Seeds and fruits: Not observed to date.

Disease/pest resistance: Neither resistance nor susceptibility to normal diseases and pests of *Hibiscus syriacus* have been observed.

Garden performance: Good tolerance, performs well in humid conditions.

Temperature tolerance: Low temperature tolerance to at least USDA zone 4, high temperature tolerance to at least 40° C.

What is claimed is:

1. A new and distinct cultivar of *Hibiscus* plant named 'SUMMER NIGHT' as herein illustrated and described.

* * * * *